United States Patent [19]

Ducret et al.

[11] 4,139,616
[45] Feb. 13, 1979

[54] FUNGICIDAL COMPOSITIONS BASED ON PHOSPHOROUS ACID ESTERS AND SALTS THEREOF

[75] Inventors: Jacques Ducret; Guy Lacroix, both of Lyon; Jean-Michel Gaulliard, Orlienas, all of France

[73] Assignee: PEPRO, France

[21] Appl. No.: 531,387

[22] Filed: Dec. 10, 1974

[30] Foreign Application Priority Data

Dec. 14, 1973 [FR] France .................. 73 45627

[51] Int. Cl.² .................................. A01N 9/36
[52] U.S. Cl. ............................ 424/222; 424/218; 424/219; 424/223
[58] Field of Search ................. 424/222; 260/961

[56] References Cited

U.S. PATENT DOCUMENTS 2,792,374  5/1957  Bradley et al. ................. 260/961

FOREIGN PATENT DOCUMENTS 1334850  10/1973  United Kingdom.

OTHER PUBLICATIONS

Chemical Abstracts, 72: 85774q (1970).
J. Organic Chem., Orlovskii et al. (1972), vol. 42, p. 1924.

*Primary Examiner*—Leonard Schenkman
*Attorney, Agent, or Firm*—Robert E. Burns; Emmanuel J. Lobato; Bruce L. Adams

[57] ABSTRACT

Compositions for controlling fungus disease are disclosed which contain as active material a fungicidally effective amount of at least one compound of the formula

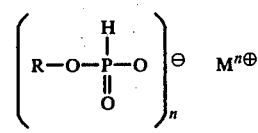

in which R is an optionally halogenated or nitrated, linear or branched alkyl radical containing from 1 to 18 carbon atoms and preferably from 1 to 8 carbon atoms, an optionally halogenated alkenyl or alkinyl radical, an alkoxy alkyl radical, an alkenoxy alkyl radical, the hydrocarbon portion of these four types of radicals containing from 1 to 8 and preferably from 1 to 5 carbon atoms, a cyclohexyl radical, an optionally substituted aryl radical, preferably phenyl, or aryl alkyl radical, preferably phenyl alkyl, or even a heterocyclic radical optionally attached to the oxygen through an aliphatic chain, preferably tetrahydrofurfuryl, M represents an ammonium cation, ammonium substituted by 1 to 4 alkyl or hydroxy alkyl radicals containing from 1 to 5 carbon atoms or by 1 to 2 cyclohexyl radicals or a phenyl radical, or a cation of a metal from the group comprising the alkali metals, preferably sodium and potassium, alkaline earth metals, preferably magnesium, barium, calcium, and polyvalent metals such as, preferably, zinc, manganese, copper(I) and (II), iron, nickel, aluminium, n is an integer equal to the valency of M.

29 Claims, No Drawings

FUNGICIDAL COMPOSITIONS BASED ON PHOSPHOROUS ACID ESTERS AND SALTS THEREOF

This invention relates to fungicidal compositions based on monoesters of phosphorous acid (or phosphites) and their salts. These compounds are sometimes also referred to as monoalkyl (aryl ...) phosphites.

More particularly, the invention relates to compositions which are suitable for use in controlling parasitic fungi in plants and which contain, as their active material, at least one compound corresponding to the general formula:

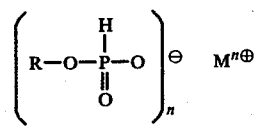

in which

R is an optionally halogenated or nitrated, linear or branched alkyl radical containing from 1 to 18 carbon atoms and preferably from 1 to 8 carbon atoms, an optionally halogenated alkenyl or alkinyl radical, an alkoxy alkyl radical, an alkenoxy alkyl radical, the hydrocarbon portion of these four types of radicals containing from 1 to 8 and preferably from 1 to 5 carbon atoms, a cyclohexyl radical, an optionally substituted aryl radical, preferably phenyl, or aryl alkyl radical, preferably phenyl alkyl, or even a heterocyclic radical optionally attached to the oxygen through an aliphatic chain, preferably tetrahydrofurfuryl, M represents an hydrogen atom ammonium cation, ammonium substituted by 1 to 4 alkyl or hydroxy alkyl radicals containing from 1 to 5 carbon atoms or by 1 to 2 cyclohexyl radicals or a phenyl radical, or a cation of a metal from the group comprising the alkali metals, preferably sodium and potassium, alkaline earth metals, preferably magnesium, barium, calcium, and polyvalent metals such as, preferably, zinc, manganese, copper(I) and (II), iron, nickel, aluminum, n is an integer equal to the valency of M.

Some of these compounds are known per se. V. V. Orlovski et al, Journal of Gen. Chem. USSR, Vol. 42, p. 1924 (1972) describe the preparation of numerous salts of monoalkyl phosphites and, in particular, monoethyl phosphites with metallic or ammonium cations substituted to a greater or lesser extent, although they do not mention the fact that these compounds have fungicidal properties.

It has now been found that the compounds according to the invention show excellent fungicidal properties, especially with respect to various types of mildew, such as mildew of the vine, tobacco mildew and hop mildew.

These compounds may be obtained by the following general methods (cf. Houben-Weyl, Vol. XII/2).

First of all, phosphites may be prepared by transesterifying a dialkyl phosphite with phosphorous acid (E. E. NIFANTEV, L. P. LEVITAN, C.A. 1107e 1966) in accordance with the following scheme:

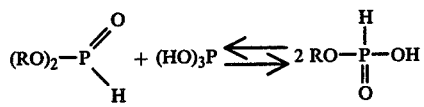

O-ethyl phosphite was prepared by this process: an equimolecuar mixture of O,O-diethyl phosphite and phosphorous acid is heated for 6 hours to 150° C. A liquid of index $n_D^{20} = 1.4211$ and of density $d = 1.0043$ (20° C.) is obtained in a quantitative yield.

The following compounds may also be prepared by this method: O-methyl phosphite, O-n-hexyl phosphite, O-isooctyl phosphite, O-n-nonyl phosphite, O-n-decyl phosphite, O-n-dodecyl phosphite, O-n-hexadecyl phosphite, O-cyclohexyl phosphite, O-phenyl phosphite, O-benzyl phosphite.

It is also possible to obtain (cf. Houben-Weyl, Vol. XII/2, page 6) esters according to the invention by hydrolyzing a phosphorous acid dichloride with two equivalents of water in accordance with the following scheme:

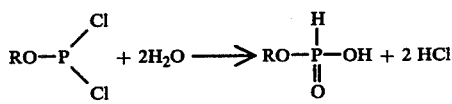

O-octyl phosphite in particular may be prepared by this method.

So far as the salts are concerned, they may be prepared by at least two methods: the first (cf. Houben-Weyl, Vol, XII, page 7) comprises hydrolyzing or saponifying an O,O-dialkyl phosphite in accordance with the following scheme:

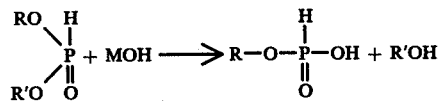

This method is particularly suitable for alkali metal salts and ammonium salts.

I - Alkali metal and ammonium salts

Saponification is carried out with a mineral or organic base in aqueous solution. The reaction takes place in 1 to 4 hours at a temperature ranging from ambient temperature to the reflux temperature (aqueous medium). The products obtained, which are liquids or solids generally soluble in water, are separated by eliminating the water and the solvent, if any.

Sodium O-ethyl phosphite was prepared in this way. One equivalent of soda in hydroalcoholic solution is added dropwise with stirring to a hydroalcoholic solution of O,O-diethyl phosphite. After standing for 2 hours, the alcohol and water are removed by distillation under reduced pressure in a water bath. The solid residue is recrystallized from absolute alcohol.

Melting point: > 300° C., yield: 68%.

| Analysis for $C_2H_6O_3Na P$ % | C | H | P |
|---|---|---|---|
| Calculated | 18.18 | 4.54 | 23.45 |
| Found | 18.18 | 4.63 | 23.38 |

The following salts were prepared by this method:

| | | |
|---|---|---|
| sodium O-methyl phosphite | m.p. | 125° C |
| sodium O-n-propyl phosphite | m.p. | 195–196° C |
| sodium O-isopropyl phosphite | m.p. | 132–133° C |
| sodium O-n-butyl phosphite | m.p. | 178° C |
| sodium O-n-octyl phosphite | m.p. | 167° C |
| sodium O-n-dodecyl phosphite | m.p. | 100° C |
| sodium O-n-hexadecyl phosphite | m.p. | 52° C |

The ammonium salts are obtained in the following manner illustrated for ammonium O-ethyl phosphite:

0.036 mole of O,O-diethyl phosphite are dissolved in a 25% aqueous ammonia solution. After standing for 1 hour, the solution is evaporated under reduced pressure in a water bath. The initially rubbery and colorless residue crystallized. Crystals in the form of colorless needles are obtained by crystallization in a mixture of ethanol and acetone.

Yield: 87%, m.p.: 99°–100° C.

| Analysis for $C_2H_{10}NO_3P$ | | | | |
|---|---|---|---|---|
| % | C | H | N | P |
| Calculated | 18.90 | 7.87 | 11.02 | 24.41 |
| Found | 18.93 | 7.90 | 11.10 | 24.29 |

Other alkali metal salts, whose characteristics and, where necessary, the particular preparation conditions are shown in the following Tables 1 and 1A, were obtained by changing the saponification base and/or the alkyl radical in the procedure described above:

Table 1

$$R-O-\overset{H}{\underset{\underset{O}{\|}}{P}}-O^{\ominus}NH_4^{\oplus}$$

| Compound | Empirical formula | Physical constants | Yield | Centesimal analysis % Calculated | Found |
|---|---|---|---|---|---|
| $CH_3-\overset{CH_3}{\underset{CH_3}{\overset{\|}{C}}}-O-\overset{H}{\underset{\underset{O}{\|}}{P}}-O^{\ominus}NH_4^{\oplus}$ | $C_4H_{14}NO_3P$ | PF 164.5° | 62% | C 31.00<br>H 9.03<br>N 9.03<br>P 20.00 | 31.04<br>9.05<br>9.18<br>20.13 |
| $\underset{C_2H_5}{\overset{n\,C_4H_9}{\diagdown}}CH-CH_2-O-\overset{H}{\underset{\underset{O}{\|}}{P}}-O^{\ominus}NH_4^{\oplus}$ | $C_8H_{22}NO_3P$ | — | 82% | C 45.50<br>H 10.43<br>N 6.64<br>P 14.69 | 44.26<br>10.08<br>6.79<br>16.10 |
| $CH_3-(CH_2)_5-O-\overset{H}{\underset{\underset{O}{\|}}{P}}-O^{\ominus}NH_4^{\oplus}$ | $C_6H_{18}NO_3P$ | — | 34% | C 39.30<br>H 9.85<br>N 7.65<br>P 16.92 | 37.19<br>9.80<br>7.78<br>17.89 |
| $ClCH_2-CH_2-O-\overset{H}{\underset{\underset{O}{\|}}{P}}-O^{\ominus}NH_4^{\oplus}$ | $C_2H_9ClNO_3P$ | | 62% | C 14.87<br>H 5.57<br>N 8.67<br>P 19.20 | 14.78<br>5.69<br>8.70<br>19.19 |
| $CH_3O-CH_2-CH_2-O-\overset{H}{\underset{\underset{O}{\|}}{P}}-O^{\ominus}NH_4^{\oplus}$ | $C_3H_{12}NO_4P$ | PF 56.5° | 79% | C 22.93<br>H 7.65<br>N 8.92<br>P 19.75 | 22.87<br>7.65<br>8.89<br>19.90 |
| $CH_3O-\overset{H}{\underset{\underset{O}{\|}}{P}}-O^{\ominus}NH_4^{\oplus}$ | $CH_8NO_3P$ | hygroscopic product | 79% | C 10.62<br>H 7.08<br>N 12.39<br>P 27.43 | 10.76<br>7.02<br>12.37<br>27.30 |
| $CH_3-CH_2-CH_2-O-\overset{H}{\underset{\underset{O}{\|}}{P}}-O^{\ominus}NH_4^{\oplus}$ | $C_3H_{12}NO_3P$ | hygroscopic product | 100% | C 25.53<br>H 8.51<br>N 9.93<br>P 21.99 | 25.76<br>8.66<br>9.93<br>21.67 |
| $\underset{CH_3}{\overset{CH_3}{\diagdown}}CH-O-\overset{H}{\underset{\underset{O}{\|}}{P}}-O^{\ominus}NH_4^{\oplus}$ | $C_3H_{12}NO_3P$ | hygroscopic product m.p.: 131° C. | 31% | C 25.53<br>H 8.51<br>N 9.93<br>P 21.99 | 25.71<br>8.76<br>9.98<br>21.96 |
| $CH_3-CH_2-CH_2-CH_2-O-\overset{H}{\underset{\underset{O}{\|}}{P}}-O^{\ominus}NH_4^{\oplus}$ | $C_4H_{14}NO_3P$ | hygroscopic product | 81% | C 30.97<br>H 9.03<br>N 9.03<br>P 20.00 | 30.94<br>9.03<br>8.94<br>20.10 |
| $\underset{CH_3}{\overset{CH_3}{\diagdown}}CH-CH_2-O-\overset{H}{\underset{\underset{O}{\|}}{O}}-O^{\ominus}NH_4^{\oplus}$ | $C_4H_{14}NO_3P$ | m.p. 177.5° | 99% | C 30.97<br>H 9.03<br>N 1.03<br>P 20.00 | 30.97<br>9.17<br>8.96<br>19.94 |
| $CH_2=CH-CH_2-O-\overset{H}{\underset{\underset{O}{\|}}{P}}-O^{\ominus}NH_4^{\oplus}$ | $C_3H_{10}NO_3P$ | hygroscopic product | 80% | C 25.90<br>H 7.19<br>N 10.07<br>P 22.30 | 25.83<br>7.30<br>10.10<br>22.22 |
| $CH\equiv C-CH_2-O-\overset{H}{\underset{\underset{O}{\|}}{P}}-O^{\ominus}NH_4^{\oplus}$ | $C_3H_8NO_3P$ | m.p. 69° C. soluble | 74% | C 26.20<br>H 5.84<br>N 10.20<br>P 22.60 | 26.26<br>5.84<br>10.24<br>22.53 |

Table 1-continued

| B | Empirical formula | Physical characteristics | Yield | Centesimal analysis % calculated | found |
|---|---|---|---|---|---|
| (cyclohexyl)H-O-P(H)(=O)-O⁻NH₄⁺ | C₆H₁₆NO₃P | m.p. 204° C. | 100% | C 39.78<br>H 8.84<br>N 7.74<br>P 17.13 | 39.79<br>9.14<br>7.61<br>17.20 |
| (phenyl)-O-P(H)(=O)-O⁻NH₄⁺ | C₆H₁₀NO₃P | m.p. 148° C.<br>soluble | 90% | C 41.0<br>H 5.7<br>N 17.7<br>P 8.0 | 41.19<br>5.78<br>17.69<br>8.09 |
| (phenyl)-CH₂-O-P(H)(=O)-O⁻NH₄⁺ | C₇H₁₂NO₃P | m.p. 153° C. | 41% | C 44.4<br>H 6.3<br>N 7.4<br>P 16.4 | 44.48<br>6.39<br>7.46<br>16.51 |
| (tetrahydrofuryl)-CH₂-O-P(H)(=O)-O⁻NH₄⁺ | C₆H₁₆NO₃P | m.p. 94° C. | 78% | C 32.80<br>H 7.65<br>N 7.65<br>P 16.92 | 33.29<br>7.86<br>7.26<br>15.39 |

Table 1A $$R-O-\overset{H}{\underset{\underset{O}{\parallel}}{P}}-O^- M^+$$

| B | M | Empirical formula | Physical characteristics | Centesimal analysis % calculated | found | Remarks |
|---|---|---|---|---|---|---|
| CH₃—CH₂—CH(CH₃)— | Na | C₄H₁₀NaO₃P | white hygroscopic, soluble solid | C 30.00<br>H 6.25<br>Na 14.38<br>P 19.38 | 29.84<br>6.29<br>14.29<br>19.22 | |
| (CH₃)₂CH—CH₂— | Na | C₄H₁₀NaO₃P | white hygroscopic, soluble solid | C 30.00<br>H 6.25<br>Na 14.38<br>P 19.38 | 29.84<br>6.30<br>14.13<br>19.37 | |
| CH₃O—CH₂—CH₂— | Na | C₃H₈NaO₄P | white hygroscopic, soluble solid | C 22.22<br>H 4.94<br>Na 14.20<br>P 19.14 | 22.16<br>5.05<br>14.16<br>19.20 | |
| CH₃—CH₂— | K | C₂H₆KO₃P | m.p.: 139° C. soluble | C 16.4<br>H 4.05<br>K 26.4<br>P 20.9 | 16.3<br>4.11<br>26.31<br>20.86 | Reaction with potash in hydroalcoholic solution at 45° C. |

II- Substituted ammonium salts (a) Alkanol amine and alkyl amine salts

Preparation of monoethanol ammonium O-ethyl phosphite 0.05 mole of O,O-diethyl phosphite is poured into an aqueous solution of one equivalent of monoethanolamine. The reaction is carried out for 1 hour at 50° C. Removal of the water by evaporation leaves a water-soluble oil.

Yield: 35%, $n_D^{20}$: 1.4595.

| Analysis for C₄H₁₄NO₄P % | C | H | N | P |
|---|---|---|---|---|
| Calculated | 28.1 | 8.2 | 8.2 | 18.1 |
| Found | 28.16 | 8.2 | 8.1 | 18.22 |

Similar compounds, whose characteristics are shown in the following Table 2, were prepared by the same process. The yields are in excess of 85% in every case.

Table 2

$$R-O-\overset{H}{\underset{\underset{O}{\parallel}}{P}}-O^{\ominus} \overset{\oplus}{-}\overset{|}{\underset{|}{N}}-$$

| R | —N— | Empirical formula | Physical characteristics | Centesimal analysis % calculated | found | Remarks |
|---|---|---|---|---|---|---|
| (CH₃)₂CH— | H₃NCH₃CH₂CH₂OH | C₅H₁₆NO₄P | oil<br>$n_D^{20}$ = 1.4535<br>soluble | C 32.4<br>H 8.65<br>N 7.56<br>P 16.75 | 32.20<br>9.16<br>7.44<br>16.56 | heating under reflux for 30 mins in acetonitrile |
| CH₃—CH₂— | H₂N(CH₂—CH₂OH)₂ | C₆H₁₈NO₅P | oil<br>$n_D^{20}$ = 1.4715 | C 33.5<br>H 8.38<br>N 6.83<br>P 14.4 | 33.23<br>8.29<br>6.70<br>14.27 | heating under reflux for 30 mins in water |

Table 2-continued $$R-O-\overset{\overset{\displaystyle H}{|}}{\underset{\underset{\displaystyle O}{\|}}{P}}-O^{(-)}\;{}^{(+)}-\overset{|}{\underset{|}{N}}-$$

| R | $-\overset{|}{\underset{|}{N}}-$ | Empirical formula | Physical characteristics | \% | Centesimal analysis calculated | found | Remarks |
|---|---|---|---|---|---|---|---|
| CH$_3$\\>CH—/CH$_3$ | H$_2$N(CH$_2$CH$_2$OH)$_2$ | C$_7$H$_{20}$NO$_5$P | oil $n_D^{20}$ = 1.4675 soluble | C<br>H<br>N<br>P | 36.7<br>8.74<br>6.12<br>13.5 | 34.16<br>9.03<br>5.63<br>12.39 | heating under reflux for 1.5 hours in water |
| CH$_3$CH$_2$— | HN(CH$_2$CH$_2$OH)$_3$ | C$_8$H$_{22}$NO$_6$P | m.p.: 50° C. soluble | C<br>H<br>N<br>P | 37.1<br>8.5<br>5.4<br>11.95 | 37.19<br>8.30<br>5.3<br>12.16 | heating under reflux for 1 hour in water |
| CH$_3$\\>CH—/CH$_3$ | HN(CH$_2$CH$_2$OH)$_3$ | C$_9$H$_{24}$NO$_6$P | m.p.: 40° C. | C<br>H<br>N<br>P | 39.58<br>8.8<br>5.12<br>11.3 | 39.81<br>8.98<br>5.30<br>11.11 | heating under reflux for 1.5 hours in water |
| C$_2$H$_5$— | H$_3$N—⟨⟩ | C$_8$H$_{14}$NO$_3$P | m.p.: 62° C. soluble | C<br>H<br>N<br>P | 43.7<br>6.9<br>6.9<br>15.3 | 47.26<br>7.05<br>6.96<br>15.32 | heating under reflux for 30 mins in water recrystallization from acetone |
| isoC$_3$H$_7$— | H$_3$N—⟨⟩— | C$_9$H$_{16}$NO$_3$P | m.p.: 88° C. soluble | C<br>H<br>N<br>P | 49.7<br>7.36<br>6.45<br>14.30 | 49.9<br>7.06<br>6.36<br>14.36 | heating under reflux for 4 hours in water recrystallization from toluene |
| CH$_3$—CH$_2$— | NH$_2$(CH$_3$)$_2$ | C$_4$H$_{14}$NO$_3$P | oil $n_D^{20}$ : 1.4295 soluble | C<br>H<br>N<br>P | 34.58<br>10.08<br>10.08<br>22.3 | 34.58<br>10.1<br>10.06<br>21.95 | heating to 60° C for 1 hour |

Another method or preparing alkyl ammonium salts comprises reacting an ammonium halide with a dialkyl phosphite in accordance with the following scheme:

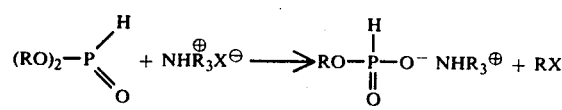

(cf. Orlovskii et. al, J. Organ. Chem. USSR, 1972, Vol. 42, pages 1924–27).

The following compounds were prepared by this method:
monoethyl ammonium O-ethyl phosphite
diethyl ammonium O-ethyl phosphite
triethyl ammonium O-ethyl phosphite (b) Quaternary ammonium salts Preparation of tetramethyl ammonium O-methyl phosphite 0.05 mole of O,O-dimethyl phosphite is added to an equivalent quantity of trimethyl amine in solution in acetone. The reaction medium is kept at 50° to 60° C. for 2 hours. Evaporation of the acetone leaves a highly hygroscopic water-soluble solid.
Yield: 77%.

| Analysis for C$_5$H$_{16}$NO$_3$P |  |  |  |  |
|---|---|---|---|---|
| % | C | H | N | P |
| Calculated | 35.5 | 9.47 | 8.28 | 18.35 |
| Found | 35.5 | 9.22 | 8.22 | 18.48 |

The corresponding O-ethyl and O-isopropyl derivatives were obtained by the same method, the O,O-dimethyl phosphite being replaced by the O-methyl-O-ethyl and the O-methyl-O-isopropyl phosphite, respectively. The reaction is carried out at 70° to 100° C. in acetonitrile. The solids obtained are recrystallized from acetone.

Tetramethyl ammonium O-ethyl phosphite

Yield: 94%; m.p.: 134° C.

| Analysis for C$_5$H$_{18}$NO$_3$P |  |  |  |  |
|---|---|---|---|---|
| % | C | H | N | P |
| Calculated | 39.4 | 9.84 | 7.65 | 16.95 |
| Found | 39.38 | 9.40 | 7.80 | 16.90 |

Tetramethyl ammonium O-isopropyl phosphite

Yield: 92%; m.p.: 153° C.

| Analysis for C$_7$H$_{20}$NO$_3$P |  |  |  |  |
|---|---|---|---|---|
| % | C | H | N | P |
| Calculated | 42.6 | 10.15 | 7.11 | 15.7 |
| Found | 42.8 | 10.26 | 7.13 | 15.9 |

III- Divalent metal salts

A metal halide is reacted with a dialkyl phosphite in accordance with the following scheme:

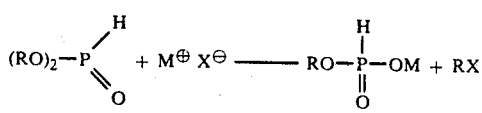

(cf. Orlovskii et. al, J. Organ. Chem. USSR, Vol. 42, pages 1924–1972).

Calcium O-ethyl phosphite was prepared in this way.

A mixture of 11 g (0.01 mole) of calcium chloride with 2.8 g (0.02 mole) of O,O-diethyl phosphite is heated with stirring for 2 hours to 110°-130° C. The mixture is then cooled. A precipitate is obtained which, after filtration and washing, gives white crystals melting at above 420° C. in a yield of 96%.

Analysis for $C_4H_{12}O_6P_2Ca$

| % | C | H |
|---|---|---|
| Calculated | 18.6 | 1.5 |
| Found | 19.12 | 1.98 |

The following salts may be similarly obtained by replacing the starting salt:
barium O-ethyl phosphite
zinc O-ethyl phosphite

Magnesium O-ethyl phosphite 0.2 mole of O,O-diethyl phosphite is added to a suspension of 0.1 mole of magnesia in 100 cc of distilled water. The exothermic reaction is carried out with stirring for 2 hours at 50° C. After filtration, the water is evaporated from the filtrate, leaving a white solid which is washed with acetone and then dried.

Yield: 100%, m.p.:> 300° C.

Analysis for $C_4H_{12}MgO_6P_2$

| % | C | H | Mg | P |
|---|---|---|----|---|
| Calculated | 19.83 | 4.96 | 10.02 | 25.63 |
| Found | 19.90 | 5.22 | 9.96 | 25.60 |

The following Table 3 shows the characteristics (appearance, melting point, solubility in water) and analysis of other metal alkyl phosphites obtained in the same way as in the preceding Example. Unless otherwise indicated, the yields are in excess of 70%, the majority being quantitative. In the case of manganese salts, the metal oxide is replaced by a carbonate.

Table 3

$$\left( R-O-\underset{\underset{O}{\overset{\overset{H}{|}}{\underset{\|}{P}}}}{}-O^{\ominus} \right)_2 M^{++}$$

| R | M | Empirical formula | Physical characteristics | Centesimal analysis | % calculated | found | Remarks |
|---|---|---|---|---|---|---|---|
| $CH_3-CH_2-CH_2-$ | Mg | $C_6H_{16}MgO_6P_2,2H_2O$ | white solid F > 300° C. soluble | C<br>H<br>Mg<br>P | 23.52<br>6.55<br>7.85<br>20.30 | 23.50<br>6.36<br>7.93<br>20.27 | |
| $CH_3\!\!\diagdown\!\!CH-$<br>$CH_3\!\!\diagup$ | Mg | $C_6H_{16}MgO_6P_2,2H_2O$ | white solid F = 126° C. | C<br>H<br>Mg<br>P | 26.62<br>5.92<br>8.9<br>22.9 | 26.6<br>5.9<br>9.1<br>22.8 | analysis expressed in dry weight reaction temperature 90° C. |
| $CH_3-(CH_2)_3-$ | Mg | $C_8H_{20}MgO_6P_2,2H_2O$ | white solid soluble | C<br>H<br>Mg<br>P | 28.74<br>7.20<br>7.20<br>18.56 | 28.70<br>7.13<br>7.37<br>18.56 | |
| $CH_3-CH_2-CH-$<br>$\quad\quad\quad\quad\;\;\,|$<br>$\quad\quad\quad\quad\;\;CH_3$ | Mg | $C_8H_{20}MgO_6P_2$ | white solid soluble | C<br>H<br>Mg<br>P | 32.21<br>6.71<br>8.05<br>20.81 | 31.99<br>6.94<br>7.98<br>20.66 | |
| $CH_3\!\!\diagdown\!\!CH-CH_2-$<br>$CH_3\!\!\diagup$ | Mg | $C_8H_{20}MgO_6P_2,H_2O$ | white solid soluble | C<br>H<br>Mg<br>P | 28.74<br>7.20<br>7.20<br>18.56 | 28.63<br>7.16<br>7.29<br>18.70 | |
| $CH_3OCH_2CH_2-$ | Mg | $C_6H_{16}MgO_8P_2$ | white solid soluble | C<br>H<br>Mg<br>P | 23.84<br>5.30<br>7.95<br>20.53 | 23.76<br>5.30<br>7.98<br>20.40 | |
| $CH_3-CH_2-CH_2-$ | Ca | $C_6H_{16}CaO_6P_2$ | white solid soluble | C<br>H<br>Ca<br>P | 25.17<br>5.59<br>13.99<br>21.68 | 24.96<br>5.90<br>13.74<br>21.56 | |
| $CH_3\!\!\diagdown\!\!CH-$<br>$CH_3\!\!\diagup$ | Ca | $C_6H_{16}CaO_6P_2$ | white solid F > 300° C. | C<br>H<br>Ca<br>P | 25.17<br>5.59<br>13.99<br>21.68 | 25.06<br>6.10<br>13.87<br>21.63 | Reaction temperature 60–70° C. |
| $CH_3-(CH_2)_3-$ | Ca | $C_8M_{20}CaO_6P_2$ | white solid soluble | C<br>H<br>Ca<br>P | 30.57<br>6.37<br>12.74<br>19.75 | 30.79<br>6.29<br>12.69<br>19.60 | |
| $CH_3-CH_2-CH-$<br>$\quad\quad\quad\quad\;\;\,|$<br>$\quad\quad\quad\quad\;\;CH_3$ | Ca | $C_8H_{20}CaO_6P_2$ | white solid soluble | C<br>H<br>Ca<br>P | 30.57<br>6.37<br>12.74<br>19.75 | 30.66<br>6.16<br>12.74<br>19.74 | |
| $CH_3\!\!\diagdown\!\!CH-CH_2-$<br>$CH_3\!\!\diagup$ | Ca | $C_8H_{20}CaO_6P_2$ | white solid soluble | C<br>H<br>Ca<br>P | 30.57<br>6.37<br>12.74<br>19.75 | 30.60<br>6.43<br>12.90<br>19.59 | |
| $CH_3OCH_2CH_2-$ | Ca | $C_6H_{16}CaO_8P_2$ | white solid soluble | C<br>H<br>Ca<br>P | 22.64<br>5.03<br>12.58<br>19.50 | 22.63<br>5.16<br>12.57<br>18.98 | |

Table 3-continued $$\left( R-O-\underset{\underset{O}{\overset{\overset{H}{|}}{P}}}{\|}-O^{\ominus} \right)_2 M^{++}$$

| R | M | Empirical formula | Physical characteristics | Centesimal analysis | % calculated | found | Remarks |
|---|---|---|---|---|---|---|---|
| $CH_3(CH_2)_3CHCH_2-$<br>\|<br>$CH_2CH_3$ | Ca | $C_{16}H_{36}CaO_6P_2,1,5H_2O$ | white solid substantially insoluble | C<br>H<br>Ca<br>P | 42.40<br>8.60<br>13.68<br>8.83 | 42.40<br>8.06<br>12.50<br>8.03 | Yield 25% |
| $CH_3-CH_2-$ | Mn | $C_4H_{12}MnO_6P_2$ | white solid<br>F = 136° C.<br>soluble | C<br>H<br>Mn<br>P | 17.6<br>4.4<br>20.1<br>22.7 | 17.4<br>4.3<br>19.9<br>22.7 | heating under reflux<br>reflux |
| $CH_3-CH_2-CH_2-$ | Mn | $C_6H_{16}MnO_6P_2$ | white solid soluble | C<br>H<br>Mn<br>P | 23.92<br>5.31<br>18.27<br>20.59 | 23.79<br>5.37<br>18.19<br>20.57 | heating under reflux |
| $CH_3$<br>\<br>CH—<br>/<br>$CH_3$ | Mn | $C_6H_{16}MnO_6P_2,2H_2O$ | white solid soluble | C<br>H<br>Mn<br>P | 21.59<br>5.94<br>16.32<br>18.40 | 21.50<br>5.60<br>16.50<br>18.32 | |
| $CH_3(CH_2)_3-$ | Mn | $C_8H_{20}MnO_6P_2$ | pale pink solid, soluble | C<br>H<br>Mn<br>P | 29.17<br>6.08<br>16.71<br>18.84 | 29.56<br>5.76<br>16.79<br>18.80 | |
| $CH_3$<br>\<br>CH—$CH_2-$<br>/<br>$CH_3$ | Mn | $C_8H_{20}MnO_6P_2,H_2O$ | pale pink solid, soluble | C<br>H<br>Mn<br>P | 27.70<br>6.34<br>15.85<br>17.88 | 27.76<br>6.12<br>15.72<br>17.78 | Yield 55% |
| $CH_3CH_2CH_2-$ | Zn | $C_6H_{16}O_6P_2Zn$ | highly viscous liquid, soluble | C<br>H<br>Zn<br>P | 23.30<br>5.17<br>21.03<br>20.06 | 23.01<br>5.16<br>21.20<br>20.16 | |
| $CH_3$<br>\<br>CH—<br>/<br>$CH_3$ | Zn | $C_6H_{16}O_6P_2Zn$ | highly viscous liquid, soluble | C<br>H<br>Zn<br>P | 23.30<br>5.17<br>21.03<br>20.06 | 23.16<br>5.06<br>21.19<br>20.03 | |

IV- Salts obtained by a double-exchange reaction (a) Synthesis via the barium salt

Zinc O-n-butyl phosphite

0.05 mole of O-n-butyl phosphite and 0.05 mole of baryta are dissolved in 150 cc of distilled water. The barium O-n-butyl phosphite is precipitated. A solution of 0.05 mole of zinc sulphate heptahydrate in 20 cc of distilled water is then added, as a result of which the barium sulphate is precipitated. It is separated by filtration or centrifuging. The clear filtrate is evaporated to dryness, giving a highly viscous liquid which is dried in vacuo. This liquid is soluble in water.

Yield: 82%.

| Analysis for $C_8H_{20}O_6P_2Zn$ | | | | |
|---|---|---|---|---|
| % | C | H | Zn | P |
| Calculated | 28.31 | 5.89 | 19.17 | 18.28 |
| Found | 28.16 | 5.96 | 19.46 | 18.28 |

The products whose characteristics are set out in the following Table 4 were obtained by changing either the alkyl radical or the metal in the procedure described above. Unless otherwise indicated, the yields are in excess of 70%.

Table 4

$$\left( R-O-\underset{\underset{O}{\overset{\overset{H}{|}}{P}}}{\|}-O^- \right)_{2\ or\ 3} M^{n+}$$

| R | M | Empirical formula | Physical Characteristics | Centesimal analysis | % calculated | found | Remarks |
|---|---|---|---|---|---|---|---|
| $CH_3CH_2CH-$<br>\|<br>$CH_3$ | $Zn^{++}$ | $C_8H_{20}O_6P_2Zn$ | highly viscous liquid, soluble | C<br>H<br>Zn<br>P | 28.31<br>5.89<br>19.17<br>18.28 | 28.16<br>5.95<br>19.54<br>18.06 | |
| $CH_3$<br>\<br>CH—$CH_2-$<br>/<br>$CH_3$ | $Zn^{++}$ | $C_8H_{20}O_6P_2Zn$ | highly viscous liquid, soluble | C<br>H<br>Zn<br>P | 28.31<br>5.89<br>19.17<br>18.28 | 28.12<br>6.03<br>19.54<br>18.19 | |

Table 4-continued $$\left( R-O-\underset{\underset{O}{\|}}{\overset{\overset{H}{|}}{P}}-O^{-} \right)_{2 \text{ or } 3} M^{n+}$$

| R | M | Empirical formula | Physical Characteristics | Centesimal analysis % | calculated | found | Remarks |
|---|---|---|---|---|---|---|---|
| $CH_3-CH_2-CH-$<br>$\quad\quad\quad\quad\quad\|$<br>$\quad\quad\quad\quad\ CH_3$ | $Mn^{++}$ | $C_8H_{20}MnO_6P_2$ | pale pink solid, soluble | C<br>H<br>Mn<br>P | 29.17<br>6.08<br>16.71<br>18.84 | 28.99<br>6.11<br>17.11<br>18.74 | |
| $CH_3OCH_2CH_2-$ | $Mn^{++}$ | $C_6H_{16}MnO_6P_2$ | solid<br>soluble | C<br>H<br>Mn<br>P | | | |
| $CH_3OCH_2CH_2-$ | $Zn^{++}$ | $C_6H_{16}ZnO_6P_2$ | solid<br>soluble | C<br>H<br>Zn<br>P | | | |
| $CH_3OCH_2CH_2-$ | $Al^{+++}$ | $C_9H_{24}Al\,O_9P_3$ | solid<br>soluble | C<br>H<br>Al<br>P | | | |
| $CH_3OCH_2CH_2$ | $Fe^{++}$ | $C_6H_{16}FeO_6P_2$ | solid<br>soluble | C<br>H<br>Fe<br>P | | | |
| $CH_3CH_2$ | $Cu^{++}$ | $C_4H_{12}CuO_6P_2$ | m.p. > 300° C. | C<br>H<br>Cu<br>P | 17.05<br>4.26<br>22.55<br>22.0 | 17.08<br>4.30<br>21.80<br>21.32 | |

(b) From the sodium salt

Aluminium O-isopropyl phosphite

Sodium O-isopropyl phosphite is prepared. A solution of 0.06 mole of aluminum nitrate with nine molecules of water in 30 cc of distilled water is added to a solution of 0.18 mole of compound in 150 cc of distilled water. The aluminum O-n-propyl phosphite is precipitated. The precipitate is centrifuged, washed with water and then with acetone and finally dried in vacuo, giving a white solid which is insoluble in water.

Yield: 60%, m.p.:> 300° C.

| Analysis for $C_9H_{24}Al\,OP_3$ % | C | H | Al | P |
|---|---|---|---|---|
| Calculated | 27.27 | 6.06 | 6.82 | 23.48 |
| Found | 27.19 | 6.28 | 6.90 | 23.50 |

The following compounds were prepared by the same method from analogous/sodium O-alkyl phosphite derivatives. The iron(III)salts were obtained by replacing the aluminum nitrate with ferric iron nitrate.

The characteristics of all these compounds are set out in the following Table 5. Unless otherwise indicated, the yields are in excess of 70%.

Table 5

$$\left( R-O-\underset{\underset{O}{\|}}{\overset{\overset{H}{|}}{P}}-O^{-} \right)_{3} M^{+++}$$

| R | $M^{+++}$ | Empirical formula | Physical characteristics | Centesimal analysis % | calculated | found | Remarks |
|---|---|---|---|---|---|---|---|
| $CH_3-CH_2-CH_2-$ | $Al^{+++}$ | $C_9H_{24}AlO_9P_3$ | white solid<br>m.p. > 300° C.<br>insoluble | C<br>H<br>Al<br>P | | | |
| $CH_3(CH_2)_3-$ | $Al^{+++}$ | $C_{12}H_{30}AlO_9P_5$ | white solid<br>m.p. > 300° C.<br>insoluble | C<br>H<br>Al<br>P | 32.88<br>6.85<br>6.16<br>21.23 | 32.69<br>6.34<br>6.18<br>20.99 | |
| $CH_3CH_2-CH-$<br>$\quad\quad\quad\quad\|$<br>$\quad\quad\quad\ CH_3$ | $Al^{+++}$ | $C_{12}H_{30}AlO_9P_3$ | white solid<br>m.p. > 300° C.<br>insoluble | C<br>H<br>Al<br>P | 32.88<br>6.85<br>6.16<br>21.23 | 32.76<br>6.98<br>6.19<br>21.19 | |
| $CH_3$<br>$\quad\ \ \backslash$<br>$\quad\quad CH-CH_2-$<br>$\quad\ \ /$<br>$CH_3$ | $Al^{+++}$ | $C_{12}H_{30}AlO_9P_3$ | white solid<br>m.p. > 300° C.<br>insoluble | C<br>H<br>Al<br>P | 32.88<br>6.85<br>6.16<br>21.23 | 32.73<br>6.94<br>6.14<br>21.24 | |
| $CH_3-CH_2-$ | $Al^{+++}$ | $C_6H_{18}AlO_9P_3$ | white solid<br>m.p. > 300° C.<br>insoluble | C<br>H<br>Al<br>P | 20.3<br>5.09<br>7.6<br>26.3 | 20.41<br>5.09<br>7.64<br>26.24 | |

Table 5-continued $$\left( R-O-\underset{\underset{O}{\overset{H}{|}}}{\overset{}{P}}-O^- \right)_{2 \text{ or } 3} M^{n+}$$

| R | $M^+$ | Empirical formula | Physical characteristics | Centesimal analysis % | calculated | found | Remarks |
|---|---|---|---|---|---|---|---|
| $CH_3-CH_2-$ | $Ni^{++}$ | $C_4H_{12}NiO_6P_2$ | m.p. > 300° C. | C<br>H<br>Ni<br>P | 17.3<br>4.3<br>27.10<br>22.4 | 15.29<br>4.63<br>21.2<br>17.87 | action of nickel bromide on sodium ethyl phosphate in absolute alcohol the product contains 11% of $NiBr_2$ |
| $CH_3-CH_2-CH_2-$ | $Fe^{+++}$ | $C_9H_{24}FeO_9P_3$ | white solid<br>m.p. > 300° C.<br>insoluble | C<br>H<br>Fe<br>P | 25.41<br>5.64<br>13.17<br>21.88 | 25.36<br>5.92<br>13.16<br>21.88 | |
| $CH_3$<br>$\phantom{CH_3}\diagdown$<br>$\phantom{CH_3\diagdown}CH-$<br>$\phantom{CH_3}\diagup$<br>$CH_3$ | $Fe^{+++}$ | $C_9H_{24}FeO_9P_3$ | white solid<br>m.p. > 300° C.<br>insoluble | C<br>H<br>Fe<br>P | 25.41<br>5.64<br>13.17<br>21.88 | 25.24<br>5.46<br>13.30<br>21.88 | |
| $CH_3-(CH_2)_3-$ | $Fe^{+++}$ | $C_{12}H_{30}FeO_9P_3$ | white solid<br>m.p. > 300° C.<br>insoluble | C<br>H<br>Fe<br>P | 30.83<br>6.42<br>11.99<br>19.91 | 30.90<br>6.10<br>12.10<br>19.88 | |

$$\left( R-O-\underset{\underset{O}{\overset{H}{|}}}{\overset{}{P}}-O^- \right)_{2 \text{ or } 3} M^{n+}$$

| R | $M^{n+}$ | Empirical formula | Physical characteristics | Centesimal analysis % | calculated | found | Remarks |
|---|---|---|---|---|---|---|---|
| $CH_3-CH_2-CH-$<br>$\phantom{CH_3-CH_2-}|$<br>$\phantom{CH_3-CH_2-}CH_3$ | $Fe^{+++}$ | $C_{12}H_{30}FeO_9P_3$ | white solid<br>m.p. > 300° C.<br>insoluble | C<br>H<br>Fe<br>P | 30.83<br>6.42<br>11.99<br>19.91 | 30.90<br>6.13<br>11.98<br>19.99 | |
| $CH_3$<br>$\phantom{CH_3}\diagdown$<br>$\phantom{CH_3\diagdown}CH-CH_2-$<br>$\phantom{CH_3}\diagup$<br>$CH_3$ | $Fe^{+++}$ | $C_{12}H_{30}FeO_9P_3$ | white solid<br>m.p. > 300° C.<br>insoluble | C<br>H<br>Fe<br>P | 30.83<br>6.42<br>11.99<br>19.91 | 30.94<br>6.12<br>12.08<br>20.01 | |

V - Iron salts

Iron O-ethyl phosphite

This compound is prepared by the method (Chem. Ber. 90, page 811) comprising reacting ferric chloride with 3 equivalents of ethyl phosphorous acid. A solid melting above 300° C. is obtained after filtration and washing.

| Analysis for $C_6H_{16}Fe\ O_9P_3$<br>% | C | H | Fe | P |
|---|---|---|---|---|
| Calculated | 18.80 | 4.70 | 14.60 | 24.3 |
| Found | 18.90 | 3.80 | 14.63 | 24.2 |

Iron O-(2-chloroethyl)-phosphite

This compound is prepared by ORLOVSKI'S method described above, replacing the soda with ferric chloride. It is possible to obtain the iron salts of the phosphites such as, for example, iron O-(2-chloroethyl)-phosphite which decomposes at around 135° C.

| Analysis for $C_6H_5Cl_3Fe\ O_9P_3$<br>% | C | H | N | P |
|---|---|---|---|---|
| Calculated | 14.8 | 3.04 | 21.9 | 19.1 |
| Found | 14.78 | 3.019 | 21.77 | 18.78 |

The following Examples illustrate the fungicidal properties of the following compounds:

1 - ammonium O-methyl phosphite
2 - ammonium O-ethyl phosphite
3 - sodium O-ethyl phosphite
4 - calcium O-ethyl phosphite
5 - ammonium O-n-propyl phosphite
6 - ammonium O-isopropyl phosphite
7 - ammonium O-n-butyl phosphite
8 - ammonium O-n-hexyl phosphite
9 - ammonium O-[(2-ethyl)-n-hexyl] phosphite
10 - sodium O-n-octyl phosphite
11 - sodium O-n-dodecyl phosphite
12- sodium O-n-hexadecyl phosphite
13- ammonium O-allyl phosphite
14- ammonium O-methoxy ethyl phosphite
15- ammonium O-cyclohexyl phosphite
16- ammonium O-benzyl phosphite
17- ammonium O-tetrahydrofurfuryl phosphite
18- sodium O-methyl phosphite
19- tetramethyl ammonium O-methyl phosphite
20- dicyclohexyl ammonium O-methyl phosphite
21- potassium O-ethyl phosphite
22- magnesium O-ethyl phosphite
23- barium O-ethyl phosphite
24- zinc O-ethyl phosphite
25- manganese O-ethyl phosphite
26- aluminum O-ethyl phosphite 27- iron(III) O-ethyl phosphite
28- copper(II) O-ethyl phosphite
29- nickel(II) O-ethyl phosphite
30- magnesium O-n-propyl phosphite
31- sodium O-isopropyl phosphite
32- calcium O-isopropyl phosphite
33- aluminum O-isopropyl phosphite
34- sodium O-n-butyl phosphite
35- calcium O-n-butyl phosphite
36- ammonium O-sec.-butyl phosphite
37- aluminum O-sec.-butyl phosphite
38- calcium O-n-[(2-ethyl)-n-hexyl] phosphite
39- sodium O-methoxy ethyl phosphite
40- magnesium O-methoxy ethyl phosphite
41- ammonium O-propargyl phosphite
42- ammonium O-phenyl phosphite EXAMPLE 1: In vivo test on Plasmopara viticola in vine plants (a) Preventive treatment The leaves of pot-grown vine plants (Gamay variety) are sprayed underneath using a spray gun with an aqueous suspension of a wettable powder having the following composition (by weight):

| | |
|---|---|
| active material to be tested | 20% |
| deflocculant (calcium lignosulphate) | 5% |
| wetting agent (sodium alkyl aryl sulphonate) | 1% |
| filler (aluminum silicate) | 74% | in the required dilution containing the active material to be tested in the required dose. Each test was repeated three times.

After 48 hours, the plants are contaminated by spraying the leaves underneath with cc of an aqueous suspension of approximately 80,000 units/cc of spores of the fungus.

The pots are then placed in an incubation cell at 20° C./100% relative humidity for a period of 48 hours.

The plants are inspected 9 days after infestation.

Under these conditions, it is found that, in a dose of 0.5 g/l, compounds 1 to 9, 11 to 22, 24, 26 to 30, 32 to 38 and 40 to 42 afford total protection, whilst compounds 23, 25, 31 and 39 afford good protection.

In addition, it was found that none of the compounds tested showed the least phytotoxicity.

(b) Treatment after contamination

The procedure is as described in (a) above, except that the plants are first of all contaminated and then treated with the active material to be tested, the plants being inspected 9 days after contamination.

Under these conditions, it was found that, in a dose of 1 g/l, compounds 1 to 8, 10 to 29, 31, 32, 36 and 40 to 42 completely stop the development of mildew on the vine plants.

(c) Systemic test by root absorption

Several vine stocks (Gamay variety) each accommodated in a pot containing vermiculite and a nutritive solution are sprinkled with 40 cc of a solution containing 0.5 g/l of the material to be tested. After 2 days, the vine is contaminated with an aqueous suspension containing 100,000 spores/cc of Plasmopara viticola. The spores are then left to incubate for 48 hours in a room at 20° C./100% relative humidity. The degree of infestation is assessed after about 9 days in relation to an infested control which has been sprinkled with 40 cc of distilled water.

Under these conditions, it was found that, in this dose of 0.5 g/l, compounds 1 to 18, 20 to 35 and 37 to 42, absorbed by the roots, afford total protection to the vine leaves against mildew, which demonstrates clearly the systemic nature of these compounds.

EXAMPLE 2: Open-air test on mildew of the vine

Groups of 5 vine stocks (Gamay variety) are sprayed every 8 days from the 5th July to the 20th August with an aqueous solution containing 200 g/hl of active material or, in one case, a wettable powder of the following composition (by weight)

| | |
|---|---|
| active material (compound) | 50% |
| calcium lignosulphate (deflocculant) | 5% |
| sodium alkyl aryl sulphonate | 1% |
| anti-lumping silica | 5% |
| kaolin (filler) | 39% |

The mildew (Plasmopara viticola) appears from 24th July onwards. Natural contamination is considerable. In August the stocks are sprayed in such a way that the leaves are kept permanently wet. The attacks of fungus are considerable and, in September, the mildew is promoted by particularly wet weather.

At the end of October, the number of mildewed areas per plot is counted on the leaves which have been effectively treated.

Under these conditions, it was found that the controls show 136 mildewed areas per plot, whereas the plots treated with compounds numbers 2, 3, 4, 21, 22, 26, 31 and 39 do not show the least sign of mildew.

In addition, the shoots which were not present during the treatments show only a few mildewed areas per plot, which adequately confirms the systemic character of these compounds under glass.

EXAMPLE 3: Test on tobacco

Groups of 5 tobacco plants (PB 91) are treated on the 15th June with a wettable powder containing 160 g/l of manebe (80%), 300 g/l of sodium O-ethyl phosphite and 300 g/l of magnesium O-ethyl phosphite (50%). One group is left untreated as control.

After 48 hours, the plants are artificially contaminated (with Peronospora tabacina) and then finely sprayed with water. The treatment is then continued once weekly.

An inspection is made on the 12th August by counting the number of mildewed areas per group. The results are set out in the following Table 6:

Table 6

| PRODUCT | Number of mildewed areas per group |
|---|---|
| Control | 48 |
| Manebe | 4 |
| Sodium O-ethyl phosphite | 2 |
| Magnesium O-ethyl phosphite | 1 |

Other tests show that the two compounds according to the invention are also effective against this fungus in curative treatment, and have a systemic action.

EXAMPLE 4: Avocado test

Your avocado plants (variety Persea indica) are planted in soil infested with Phytophtora cinnamomi, after which the soil is sprayed with a solution containing 3 g/l of aluminium O-ethyl phosphite. Some plants are left untreated as controls. Under these conditions, it was found after 20 days that the roots of the control plants are completely destroyed, whilst 90% of the roots of the treated plants are healthy.

EXAMPLE 5: Pineapple test

Young pineapple plants are contaminated with *Phytophtora parasitica*, and then treated after 48 hours by spraying with a solution containing 0.5 g/l of calcium O-ethyl phosphite. It was found after 30 days that the fungus was completely inhibited in the treated plants, whilst the controls are infested.

EXAMPLE 6: Strawberry test

Ten strawberry plants (variety Surprise des Halles) are treated by soaking for 1 hour in an aqueous solution containing 0.2% of calcium O-isopropyl phosphite, dried and then planted out, on the 14th June, in soil artificially contaminated with *Phytophtora cactorum*. Immediately afterwards and then once every 8 days until the 18th July, the plants are sprayed with the same solution which corresponds to a total application of 0.5 g of active material per plant.

Plants treated by soaking and spraying with water are used as controls.

Under these conditions, it was found on the 24th July that the protection afforded to the strawberry plants is complete, whilst 76% of the control plants are dead.

EXAMPLE 7: Pimento Test 10 pimento plants (variety Yolo wonder) which have already been planted out are transplanted on the 27th June to pots of earth artificially contaminated with *Phytophtora capsici*. The plants are sprayed immediately and then once every 8 days until the 18th July with an aqueous solution containing zinc O-ethyl phosphite so as to apply a total of 0.5 g of treatment per plant.

Plants sprayed with water are used as controls.

Under these conditions, it was found that the 10 plants are intact at the end of August, whilst the control plants have all died by 25th July.

All these Examples clearly show the remarkable fungicidal activity of the compounds according to the invention, on the one hand a systemic anti-mildew activity which both prevents and stops the development of vine mildew, and on the other hand on certain phytophtora as well.

However, they have also been found to be extremely effective in controlling other types of parasitic fungi such as *Guignardia bidwellii* in vine, *Pseudoperonospora humuli*, *Bremia lactucae*, *Phytophthora infestans*, *Peronospora* sp., *Phytophtora palmivora*, *Phytophtora phaseoli*, *Phytophtora megasperma*, *Phytophtora drechsteri* and other *Phytophtora* sp. in temperature-climate or tropical-climate plants such as tobacco, market-gardening cultures, especially onion, sweet pepper, tomato, bean, in ornamental plants, in soya, citrus, cocoa, coconut palm, hevea rubber.

Accordingly, the compounds according to the invention are particular suitable for use in the preventive or curative treatment of fungus disease in plants, especially fungus disease caused by phycomycetes and ascomycetes in the vegetables already mentioned, but also more generally in agriculture, arboriculture, horticulture, market gardening, but more especially in viticulture.

The compounds according to the invention may be used with advantage in admixture with one another or with other known fungicides, such as metal dithiocarbamates (manebe, zinebe, mancozebe,) basic salts or hydroxides of copper (oxychloride, oxysulphate), (tetrahydro)phthalimides (captane, captafol, folpel), N-(1-butyl carbamoyl)-2-benzimidazole, methyl carbamate (benomyl), 1,2-di-(3-methoxy or ethoxy)carbonyl-2-thioureido benzenes (thiophanates), methyl 2-benzimidazole carbamate, etc., either to complete the range of activity of the compounds according to the invention or to increase their persistence.

It has also been found that the compounds according to the invention may be mixed with other fungicidal, anti-mildew phosphorus derivatives, especially 2-hydroxy-1,3,2-dioxaphospholanes, $\beta$-hydroxy ethyl phosphites and phosphorous acid and its salts.

The doses in which the compounds according to the invention are used may vary within wide limits, depending both upon the virulence of the fungus and upon the climatic conditions. Doses of from 0.01 to 5 g/l of active material are generally suitable.

For their practical application, the compounds according to the invention are rarely used on their own. Instead, they generally form part of formulations which, as a rule, contain a support and/or a surfactant in addition to the active material according to the invention.

In the context of the invention, a support is an organic or mineral, natural or synthetic material with which the active material is associated to facilitate its application to the plant, to seeds or to soil, or its transportation or handling. The support can be solid (clays, natural or synthetic silicates, resins, waxes, solid fertilizers) or fluid (water, alcohols, ketones, petroleum fractions, chlorinated hydrocarbons, liquefied gases).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, soluble powders, dusting powders, granulates, solutions, emulsifiable concentrates, emulsions, suspended concentrates and aerosols.

The wettable powders according to the invention can be prepared in such a way that they contain from 20 to 95% by weight of the active material, and they normally contain, in addition to a solid support, from 0 to 5% by weight of a wetting agent, from 3 to 10% by weight of a dispersant and, when necessary, from 0 to 10% by weight of one or more stabilizers and/or other additives, such as penetration agents, adhesives or antilumping agents, colorants . . . etc.

One example of the composition of a wettable powder is given below:

| | |
|---|---|
| active material | 50% |
| calcium lignosulphate (deflocculant) | 5% |
| anionic wetting agent | 1% |
| antilumping silcia | 5% |
| kaolin (filler) | 39% |

Powders soluble in water are obtained by mixing from 20 to 95% by weight of the active material, from 0 to 10% of an antilumping agent, the remainder being a hydrosoluble filler mainly a salt.

There is one example of composition of a soluble powder:

| | |
|---|---:|
| active material | 70% |
| anionic wetting agent | 0.5% |
| antilumping silica | 5% |
| sodium sulfate (soluble filler) | 24.5% |

Aqueous dispersions and emulsions, for example compositions obtained by diluting with water a wettable powder or an emulsifiable concentrate according to the invention, are included within the general scope of the invention. These emulsions can be of the water-in-oil type or of the oil-in-water type, and can have a thick consistency resembling that of a "mayonnaise".

The compositions according to the invention can contain other ingredients, for example protective colloids, adhesives or thickeners, thixotropic agents, stabilizers or sequestrants, as well as other active materials known to have pesticidal properties, especially acaricides or insecticides.

We claim:

1. A fungicidal composition for controlling fungus disease in plants comprising as an active material, a fungicidally effective quantity of at least one compound of the formula

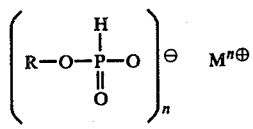

in which
R is selected from a member of the group consisting of an alkyl, halogen-substituted alkyl or nitro-substituted alkyl radical, the alkyl portion of said alkyl radicals containing from 1 to 8 carbon atoms, an alkenyl, halogen-substituted alkenyl, alkinyl, halogen-substituted alkinyl and an alkoxy-substituted alkyl radical, the hydrocarbon portion of said alkenyl, alkinyl and alkoxy-alkyl radicals containing from 2 to 5 carbon atoms,
M is selected from a member of the group consisting of an ammonium cation; ammonium substituted by a member of the group consisting of 1 to 4 alkyl or hydroxy-alkyl radicals each containing from 1 to 5 carbon atoms, 1 to 2 cyclohexyl radicals and a phenyl radical; and a cation of a metal from the group consisting of the alkali metals, alkaline earth metals, and polyvalent metals of zinc, manganese, copper (I) and (II), iron, nickel and aluminum and n is an integer equal to the valency of M in combination with an agriculturally acceptable carrier.

2. A fungicidal composition according to claim 1 which contains an inert carrier and a compatible surfactant.

3. A fungicidal composition according to claim 1 in the form of a wettable powder containing about 20 to 95% by weight of said active material, about 0 to 5% by weight of a wetting agent, from 3 to 10% by weight of a dispersant and from 0 to 10% by weight of other additives selected from the group consisting of a stabilizer, a penetration agent, an adhesive, an anti-lumping agent, a colorant and mixtures thereof, the balance being inert solid support.

4. A fungicidal composition according to claim 1 in which said composition is in the form of a soluble powder containing about 20 to 95% of said active material, 0 to 10% of an anti-lumping agent and the balance being a hydrosoluble inert solid support.

5. A fungicidal composition according to claim 1 which contains an inert solid carrier and a compatible surfactant, wherein said composition is in the form selected from a wettable powder and a soluble powder.

6. A composition as claimed in claim 1, wherein M is an ammonium cation substituted by 1 to 4 alkyl radicals or hydroxy-alkyl radicals containing from 1 to 5 carbon atoms or by 1 to 2 cyclohexyl radicals or a phenyl radical.

7. A composition as claimed in claim 1, wherein M is an alkali metal cation.

8. A composition as claimed in claim 1, wherein M is an alkaline earth metal cation.

9. A composition as claimed in claim 1, wherein M is a cation of a metal from the group comprising zinc, manganese, copper (I) and (II), iron (II) and (III) nickel and aluminum.

10. A composition as claimed in claim 1, wherein R is an alkyl radical, a halogen substituted alkyl radical containing from 1 to 4 carbon atoms, an allyl, propargyl, allyl-oxy or alkoxy-alkyl radical containing from 2 to 3 carbon atoms.

11. A composition as claimed in claim 10, wherein R is the ethyl radical.

12. A composition as claimed in claim 10, wherein R is the isopropyl radical.

13. A composition as claimed in claim 11, wherein the active material is sodium O-ethyl phosphite.

14. A composition as claimed in claim 11, wherein the active material is calcium O-ethyl phosphite.

15. A composition as claimed in claim 11, wherein the active material is aluminum O-ethyl phosphite.

16. A composition as claimed in claim 11, wherein the active material is magnesium O-ethyl phosphite.

17. A composition as claimed in claim 11, wherein the active material is zinc O-ethyl phosphite.

18. A composition as claimed in claim 11, wherein the active material is cuprous O-ethyl phosphite.

19. A composition as claimed in claim 11, wherein the active material is cupric O-ethyl phosphite.

20. A composition as claimed in claim 12, wherein the active material is sodium O-isopropyl phosphite.

21. A composition as claimed in claim 12, wherein the active material is calcium O-isopropyl phosphite.

22. A composition as claimed in claim 12, wherein the active material is aluminum O-isopropyl phosphonate.

23. A composition as claimed in claim 12, wherein the active material is magnesium O-isopropyl phosphite.

24. A composition as claimed in claim 12, wherein the active material is zinc O-isopropyl phosphite.

25. A composition as claimed in claim 12, wherein the active material is cuprous O-isopropyl phosphite.

26. A composition as claimed in claim 12, wherein the active material is cupric O-isopropyl phosphite.

27. A composition as claimed in claim 1, which additionally contains a known fungicide.

28. A fungicidal composition as claimed in claim 1 wherein R is said alkyl radical containing 1-8 carbon atoms.

29. A method for controlling fungal diseases in plants which comprises applying a fungicidally effective amount of at least one compound of the formula

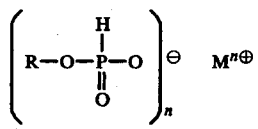

in which
R is selected from a member of the group consisting of an alkyl, halogen-substituted alkyl or nitro-substituted alkyl radical, the alkyl portion of said alkyl radicals containing from 1 to 8 carbon atoms, an alkenyl, halogen-substituted alkenyl, alkinyl, halogen-substituted alkinyl and an alkoxy-substituted alkyl radical, the hydrocarbon portion of said alkenyl, alkinyl and alkoxyalkyl radicals each containing from 2 to 5 carbon atoms, M is selected from a member of the group consisting of an ammonium cation; ammonium substituted by a member of the group consisting of 1 to 4 alkyl or hydroxyalkyl radicals each containing from 1 to 5 carbon atoms, 1 to 2 cyclohexyl radicals, and a phenyl radical; and a cation of a metal from the group consisting of the alkali metals, alkaline earth metals, and polyvalent metals of zinc, manganese, copper (I) and (II), iron, nickel and aluminum and n is an integer equal to the valency of M.

* * * * *